(12) United States Patent
Effenberger et al.

(10) Patent No.: US 7,611,886 B2
(45) Date of Patent: Nov. 3, 2009

(54) ENZYMATIC TRANSFORMATION OF A PROSTAGLANDIN (BIMATOPROST) INTERMEDIATE

(75) Inventors: Reinhard Effenberger, Haifa (IL); Ayelet Fishman, Haifa (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 362 days.

(21) Appl. No.: 11/369,518

(22) Filed: Mar. 6, 2006

(65) Prior Publication Data

US 2006/0247453 A1    Nov. 2, 2006

Related U.S. Application Data

(60) Provisional application No. 60/659,009, filed on Mar. 4, 2005.

(51) Int. Cl.
*C12P 41/00* (2006.01)
(52) U.S. Cl. .................................. 435/280; 435/198
(58) Field of Classification Search .................. None
See application file for complete search history.

(56) References Cited

U.S. PATENT DOCUMENTS 3,969,396 A    7/1976    Yankee

FOREIGN PATENT DOCUMENTS

| EP | 0 501 310 | 2/1992 |
|---|---|---|
| WO | WO 91/04337 | 4/1999 |
| WO | WO 01/55101 | 8/2001 |

OTHER PUBLICATIONS

Corey, J.A.C.S., 1969, pp. 5675, vol. 91.
Resul, et al., "Phenyl-Substituted Prostaglandins: Potent And Selective Antiglaucoma Agents", *J. Med. Chem.*, 1993, pp. 243-248, vol. 36.
Fox et al., "An Enantioconvergent Synthesis of (R)-4-Aryloxy-1-butyne-3-ols for Prostanoid Side Chains", Adv. Synth. Catel. (344) 50-56 (2000).
Taber et al., "Total Synthesis of the Four Enantiomerically Pure Diastereomers of $8\text{-}F_{2t}$ Isoprostane", J. Org. Chem. (66) 1876-1884(2001).
Chen et al., "Preparation of optically Active Tertiary Alcohols by Enzymatic Methods. Application to the Synthesis of Drugs and natural Products", J. Org. Chem. (62) 4349- 4357 (1997).
English Translation of Office Action for Application, JP2007-511732, pp. 1-7, not fully considered due to lack of documents therein.

*Primary Examiner*—Sandra Saucier
*Assistant Examiner*—Susan Hanley
(74) *Attorney, Agent, or Firm*—Kenyon & Kenyon LLP

(57) ABSTRACT

A method for the selective enzymatic acetylation of a bimatoprost intermediate is provided.

31 Claims, 1 Drawing Sheet

ENZYMATIC TRANSFORMATION OF A PROSTAGLANDIN (BIMATOPROST) INTERMEDIATE

RELATED APPLICATION

This application claims the benefit of U.S. provisional application No. 60/659,009, filed Mar. 4, 2005; herein incorporated by reference.

FIELD OF THE INVENTION

The present invention relates to the prostaglandin bimatoprost. In particular, the invention is directed to a method for the selective enzymatic acetylation or alcoholysis of a bimatoprost intermediate.

BACKGROUND OF THE INVENTION

Bimatoprost, (5Z)-7-[(1R,2R,3R,5S)-3,5-Dihydroxy-2-[1E,3S)-3-hydroxy-5-phenyl-1-pentenyl]cyclopentyl]-5-N-ethylheptenamide, is a synthetic derivative of prostaglandin $PGF_2$. It is indicated for intraocular pressure regulation and treatment of open angle glaucoma, and is available from the innovator Allergan, Inc. as LUMIGAN®.

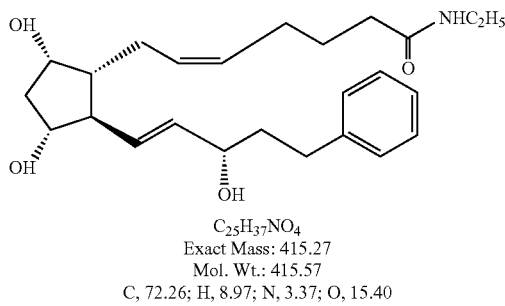

$C_{25}H_{37}NO_4$
Exact Mass: 415.27
Mol. Wt.: 415.57
C, 72.26; H, 8.97; N, 3.37; O, 15.40

The (S)-I intermediate, (1S,5R,6R,7R)-6-[(3S)-3-hydroxy-5-phenyl-1-pentenyl]-7-[(4-benzoyl)oxy]-2-oxabicyclo[3,3,0]octan-3-one,

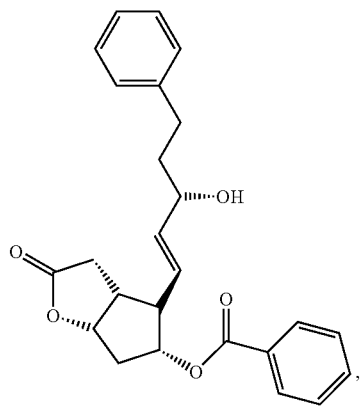

compound (S)-I, is one of a pair of epimers, and, thus, differs in configuration from the corresponding (R)-I compound, (1S,5R,6R,7R)-6-[(3R)-3-hydroxy-5-phenyl-1-pentenyl]-7-[(4-benzoyl)oxy]-2-oxabicyclo[3,3,0]octan-3-one,

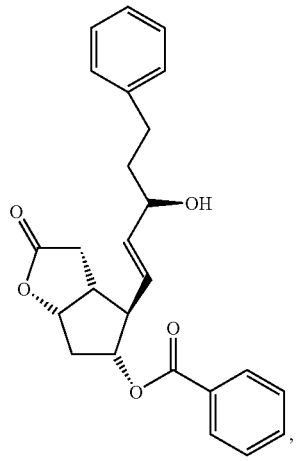

compound (R)-I, at only one asymmetric carbon, the carbon at the 3 position.

In the preparation of bimatoprost, only the (S)-I intermediate, leads to the active form of the drug. In one example, U.S. Pat. No. 3,969,396 discloses the following process for the synthesis of bimatoprost:

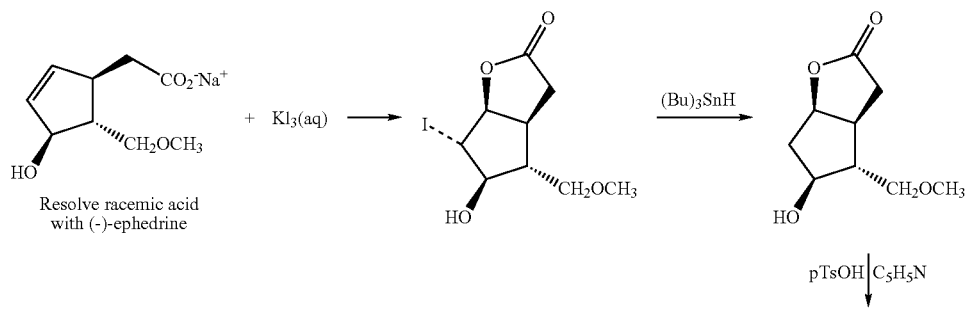

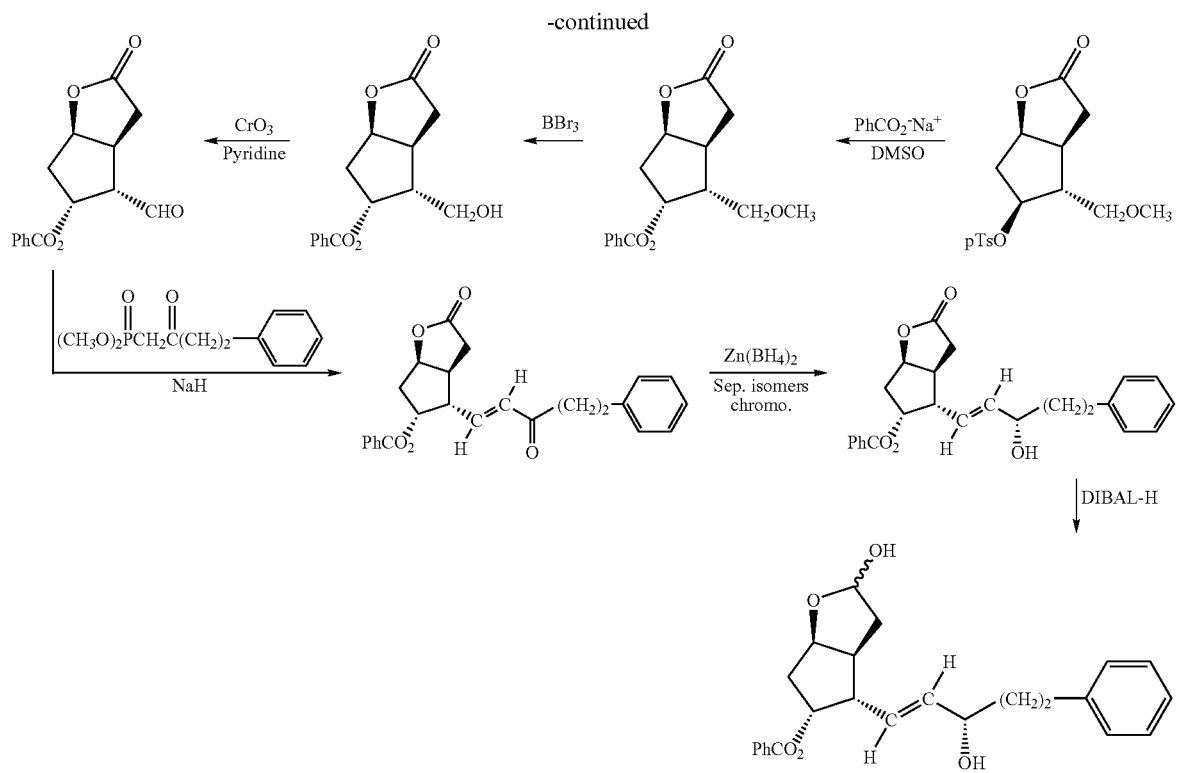

There are a number of methods used to obtain the required stereochemistry, such as by chromatography and crystallization. Currently, the most widely practiced method of separation of diastereomeric mixtures in the case of the (S)-I intermediate is via chromatography. However, this stereoselective synthesis is still an unfavorable process for scale up due to its multi-step nature and cost. The difficulty in chromatographic separation stems from the fact that the two epimers do not differ greatly in their affinity, and, thus, their retention times are too close to allow efficient separation in one chromatographic step, especially on large scale. Therefore, a process for the separation of the (S)-I intermediate from a mixture of the epimers is highly desirable. The present invention provides such a process by greatly improving the efficacy of chromatographic separation.

SUMMARY OF THE INVENTION

The invention is directed to methods for the selective conversion, preferably acetylation or alcoholysis, of an (R) epimer of a bimatoprost intermediate in the presence of an enzyme, preferably a lipase enzyme. The (R) epimer is selected from the group consisting of (R)-I, (1S,5R,6R,7R)-6-[(3R)-3-hydroxy-5-phenyl-1-pentenyl]-7-[(4-benzoyl)oxy]-2-oxabicyclo[3,3,0]octan-3-one, and (R)-III, (1S,5R,6R,7R)-6-[(3R)-3-acetoxy-5-phenyl-1-pentenyl]-7-[(4-benzoyl)oxy]-2-oxabicyclo[3,3,0]octan-3-one, and the (S) epimer is selected from the group consisting of (S)-I, (1S,5R,6R,7R)-6-[(3S)-3-hydroxy-5-phenyl-1-pentenyl]-7-[(4-benzoyl)oxy]-2-oxabicyclo[3,3,0]octan-3-one, and (S)-III, (1S,5R,6R,7R)-6-[(3S)-3-acetoxy-5-phenyl-1-pentenyl]-7-[(4-benzoyl)oxy]-2-oxabicyclo[3,3,0]octan-3-one. Where the (R) epimer is (R)-I, the (S) epimer is (S)-I, and only the (R)-I epimer is acetylated to the acetylated compound (R)-III, in the presence of an acetylating agent. Where the (R) epimer is (R)-III, the (S) epimer is (S)-III, and the (R)-III epimer is preferably converted to (R)-I by alcoholysis in the presence of a $C_{1-6}$ alcohol.

In a further embodiment, the invention is directed to a process for the preparation of bimatoprost comprising:
(a) selectively converting an (R) epimer in a mixture comprising the (R) and (S) epimers,
(b) obtaining the (S)-I intermediate by recovering the (S)-I intermediate or, alternatively, recovering the (S)-III intermediate, and then converting the (S)-III intermediate to the (S)-I intermediate; and
(c) converting the (S)-I intermediate to bimatoprost.

DETAILED DESCRIPTION OF THE INVENTION

Figure 1:
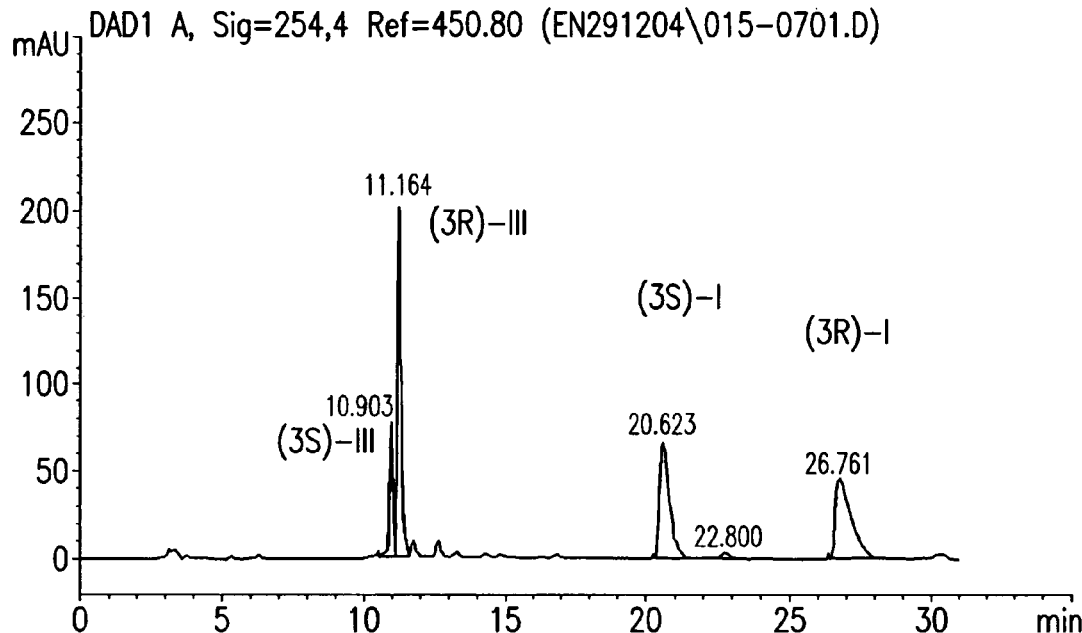
FIG. 1 illustrates an HPLC chromatogram of a mixture of (R)-I, (R)-III, (S)-I, and (S)-III.

As used herein, the term "(S)-I" refers to the compound (1S,5R,6R,7R)-6-[(3S)-3-hydroxy-5-phenyl-1-pentenyl]-7-[(4-benzoyl)oxy]-2-oxabicyclo[3,3,0]octan-3-one.
As used herein, the term "(S)-III" refers to the compound (1S,5R,6R,7R)-6-[(3S)-3-acetoxy-5-phenyl-1-pentenyl]-7-[(4-benzoyl)oxy]-2-oxabicyclo[3,3,0]octan-3-one.
As used herein, the term "(R)-I" refers to the compound (1S,5R,6R,7R)-6-[(3R)-3-hydroxy-5-phenyl-1-pentenyl]-7-[(4-benzoyl)oxy]-2-oxabicyclo[3,3,0]octan-3-one.
As used herein, the term "(R)-III" refers to the compound (1S,5R,6R,7R)-6-[(3R)-3-acetoxy-5-phenyl-1-pentenyl]-7-[(4-benzoyl)oxy]-2-oxabicyclo[3,3,0]octan-3-one.
As used herein, the term "reduced (R)-I" refers to the compound (1S,5R,6R,7R)-6-[(3R)-3-hydroxy-5-phenyl-pentanyl]-7-[(4-benzoyl)oxy]-2-oxabicyclo[3,3,0]octan-3-one.

As used herein, the term "reduced (R)-III" refers to the compound (1S,5R,6R,7R)-6-[(3R)-3-acetoxy-5-phenyl-pentanyl]-7-[(4-benzoyl)oxy]-2-oxabicyclo[3,3,0]octan-3-one.

As used herein, the term "reduced (S)-III" refers to the compound (1S,5R,6R,7R)-6-[(3S)-3-acetoxy-5-phenyl-1-pentenyl]-7-[(4-benzoyl)oxy]-2-oxabicyclo[3,3,0]octan-3-one.

As used herein, the term "reduced (S)-I" refers to the compound (1S,5R,6R,7R)-6-[(3S)-3-hydroxy-5-phenyl-pentanyl]-7-[(4-benzoyl)oxy]-2-oxabicyclo[3,3,0]octan-3-one.

As will be recognized to those skilled in the art, (S)-I and (R)-I are epimers, as are (S)-III and (R)-III. That is, (S)-I differs in configuration from (R)-I, and (S)-III differs in configuration from (R)-III at only one of the asymmetric carbons, the carbon at the 3 position. The configurations of all other equivalent asymmetric carbons are the same in each of the compounds. The assignment of the absolute configurations of the compounds is based on analogy with the p-phenylbenzoyl derivatives of compounds I and III, as determined by Resul et al., *J. Med. Chem.* 36:243-248, 1993.

As used herein, the terms "enzymatic" and "enzymatically" mean that the respective process is performed with an enzyme. Preferred enzymes are lipases. The enzymes can be crude or immobilized. Procedures for immobilizing enzymes are well known in the art.

The process of the present invention is directed to methods for the selective conversion, preferably acetylation or alcoholysis, of an (R) epimer of a bimatoprost intermediate in the presence of a lipase enzyme. The method of the invention is highly selective, such that, preferably, in a mixture of (S)-I intermediate or (S)-III and its (R) epimer, only the (R) epimer is converted.

In one embodiment of the present invention, preferably in a process for the preparation of bimatoprost, the invention is directed to the selective conversion of an (R) epimer in a mixture comprising (R) and (S) epimers, in the presence of an enzyme. The (R) epimer is selected from the group consisting of (R)-I and (R)-III while the (S) epimer is selected from the group consisting of (S)-I and (S)-III.

In one aspect of this embodiment, the (R) epimer comprises primarily (R)-I, the (S) epimer comprises primarily (S)-I, and the (R)-I epimer is preferably converted to (R)-III by acetylation in the presence of an acetylating agent. Preferably, in accordance with the invention, a mixture comprising (S)-I and (R)-I in any ratio is mixed with an acetylating agent, an organic solvent, and an enzyme, where the acetylating agent may also be used as the solvent. The acetylation reaction of the invention proceeds according to the following reaction scheme:

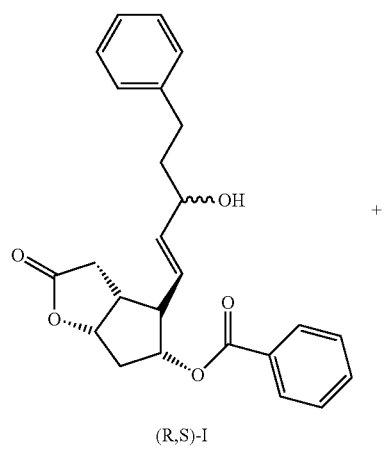

(R,S)-I

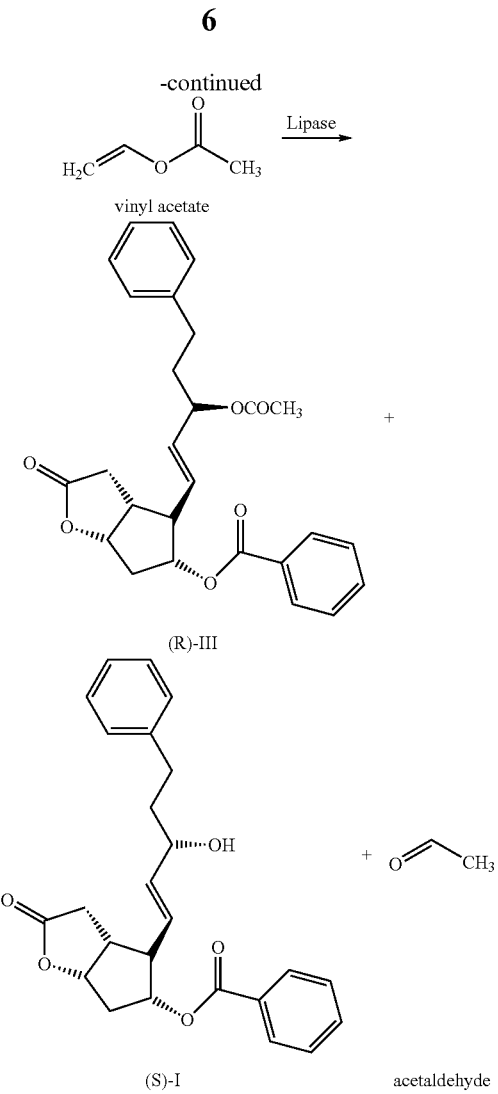

Preferably, the substrates, reactants, and reaction conditions for the acetylation are as follows. The (R,S)-I substrate may contain the (R)-I and (S)-I epimers in any relative amount and in any concentration up to the solubility limit in the solvent. Preferably, the substrate is present in the solvent in an amount of from about 0.1 to about 20 weight/volume percent, preferably from about 0.1 to about 3 weight/volume percent. Reduced (R)-I, i.e., (R)-I without the double bond, may also be used as the substrate.

Useful acetylating agents include, but are not limited to a $C_2$-$C_6$ alkyl acetate, $C_2$-$C_6$ alkenyl acetate or $C_5$-$C_8$ benzoyl acetate preferably vinyl acetate, ethyl acetate, ethylphenyl acetate, butyl acetate, vinyl butyrate, vinyl propionate and vinyl benzoate, where vinyl acetate is most preferred. The mole ratio of acetylating agent to substrate preferably ranges from substantially stoichiometric, i.e., 1:1, to infinite, where the acetylating agent may be used as the solvent. More preferably, the mole ratio of acetylating agent to substrate is from about 2:1 to about 3:1.

The resulting mixture is stirred, preferably at a temperature of from about 10° to about 70° C., more preferably, from about 25° to 55° C., such that the reaction may be conducted at room temperature. Depending on the temperature used, the time period will range between about 10 and about 100 hours, more preferably, from about 24 to about 60 hours, and, most preferably, from about 24 to about 52 hours. The reaction type may be batch or column.

More preferably, the (S)-I from the original reaction mixture remains substantially unreacted, such that there is 0% to 10% conversion, preferably 0% to 5% conversion, more preferably 0% to 2% conversion, and most preferably about no conversion. Preferably, the resulting reaction mixture will contain (R)-III in a high yield of about 40% to about 50%, more preferably about 45% to about 50% yield.

In another aspect of this embodiment, the (R) epimer is (R)-III, the (S) epimer is (S)-III, and the (R)-III epimer is preferably converted to (R)-I by alcoholysis, proceeding according to the following scheme:

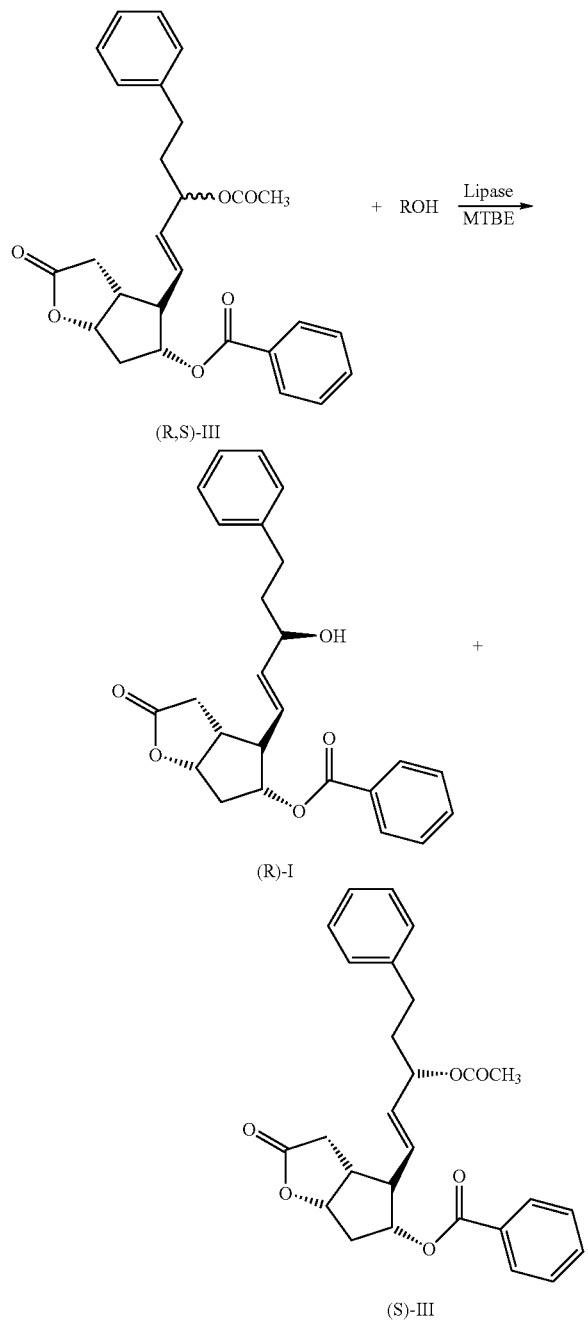

in the presence of a $C_{1-6}$ alcohol, preferably $C_{2-5}$ alcohol, and most preferably butanol or ethanol. The resulting mixture is then stirred, preferably, for from about 24 to about 250 hours. Preferably, the mixture is stirred at a temperature of from about 10° to about 70° C.

Preferably, the resulting reaction mixture will contain (R)-I in a high yield of about 40% to about 50%, more preferably about 45% to about 50% yield. More preferably, the (S)-III from the original reaction mixture remains substantially unreacted, such that there is 0% to 10% conversion, preferably 0% to 5% conversion, more preferably 0% to 2% conversion, and, most preferably, about no conversion. The selective alcoholysis allows the (S)-III to be separated from the (R)-I compound by a simple chromatographic separation. In accordance with the present invention, only the (R)-enantiomer reacts leading to formation of (R)-I. Subsequently, the S-III is easily separated from R-I, and can be then be hydrolyzed to produce S-I.

Preferably, in both the acetylation and alcoholysis, the enzyme is from microorganisms such as *Candida antarctica, Pseudomonas* sp., *Pseudomonas cepacia, Alcaligenes* sp., *Pseudomonas stutzeri, Candida antarctica, Candida rugosa, Aspergillus niger, Mucor meihei*, as well as other lipases of microbial, mammalian, and plant origin. More preferably, the enzyme is *Pseudomonas stutzeri* lipase or *Alcaligenes* sp lipase.

Useful solvents in both the acetylation and alcoholysis include, but are not limited to, $C_2$ to $C_8$ linear, branched or cyclic ether, preferably $C_2$ to $C_6$ ether, $C_2$ to $C_8$ ketone, preferably $C_2$ to $C_4$ ketone, chlorinated $C_1$ to $C_4$ hydrocarbons, and tri($C_1$-$C_6$ alkyl)silyl groups, where methyl tert-butyl ether (MTBE), diisopropyl ether, methyl ethyl ketone, dichloromethane, tetrachloromethane, acetone, methyl isobutyl ketone (MIBK), and THF, are more preferred, and MTBE and methyl ethyl ketone are most preferred.

Whatever the selective conversion, the enzyme is then separated by a suitable means, as will be known to the skilled artisan, for example by filtration or centrifugation to mention just two, and the filtrate is concentrated.

Because of the new, much larger difference in the polarity between the alcohol form and the ester form, for example, in the case of selective acetylation of the (R)-I intermediate to the (R)-III intermediate in a mixture comprising (R)-I and (S)-I, the selectively esterified epimers or the epimers selectively subjected to alcoholysis now have well resolved elution times, thereby allowing the complete separation of the mixtures, however prepared, in a single-pass by, for example, column chromatography.

In a further embodiment, the invention is directed to a process for the preparation of bimatoprost, comprising:
a. selectively converting of the (R)-I, (1S,5R,6R,7R)-6-[(3R)-3-hydroxy-5-phenyl-1-pentenyl]-7-[(4-benzoyl)oxy]-2-oxabicyclo[3,3,0]octan-3-one to (R)-III, (1S,5R,6R,7R)-6-[(3R)-3-acetoxy-5-phenyl-1-pentenyl]-7-[(4-benzoyl)oxy]-2-oxabicyclo[3,3,0]octan-3-one in accordance with the invention;
b. recovering (S)-I; and
c. converting (S)-I into bimatoprost.

In a further embodiment, the invention is directed to a process for the preparation of bimatoprost, comprising:
a. selective converting (R)-III, (1S,5R,6R,7R)-6-[(3S)-3-acetoxy-5-phenyl-1-pentenyl]-7-[(4-benzoyl)oxy]-2-oxabicyclo[3,3,0]octan-3-one to (R)-I, (1S,5R,6R,7R)-6-[(3R)-3-hydroxy-5-phenyl-1-pentenyl]-7-[(4-benzoyl)oxy]-2-oxabicyclo[3,3,0]octan-3-one in accordance with the invention;
b. recovering (S)-III;
c. converting (S)-III into (S)-I; and
d. converting (S)-I into bimatoprost The (S)-I may be converted into bimatoprost by any means known in the art, such as that disclosed in Corey, E. J., J.A.C.S., 91 5675 (1969). The separated (S)-III (ester) may be converted into the desired (S)-I (alcohol) by methods well known to those skilled in the art.

It should be apparent to anyone skilled in the art that the process of the present invention can be applied to a mixture of reduced (R)-I and reduced (S)-I intermediate, Reduced (S)-I

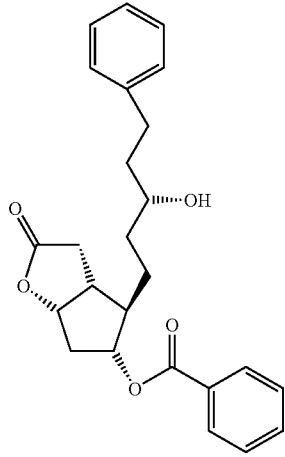

Reduced (R)-I

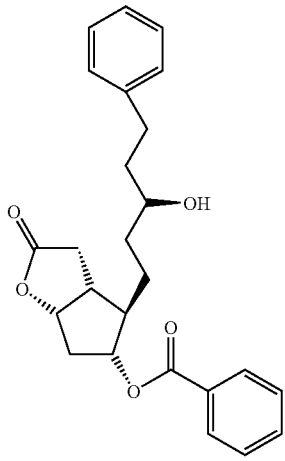

so as to selectively recover reduced (S)-I by acetylation of the reduced (R)-I to form (R)-III which may be useful in the process for preparation for example, of other prostaglandins.

EXAMPLES

The following non-limiting examples are merely illustrative of the preferred embodiments of the present invention, and are not to be construed as limiting the invention, the scope of which is defined by the appended claims.

Example 1

Selective Acetylation of (S)-I and (R)-I Epimers Using *Pseudomonas stutzeri* Lipase The selective acetylation of the (S)-I and (R)-I epimers was carried out by introducing 10 mg (0.025 mmol) of a mixture, containing equimolar amounts of (S)-I and (R)-I, the C3 epimers of compound I, into a vial with 0.3 ml (3.2 mmol) of vinyl acetate, 6 ml of MTBE, and 100 mg of *Pseudomonas stutzeri* lipase (TL, Meito Sangyo, Japan). The resulting batch mixture was stirred at room temperature for 46 hours. Analysis of the stirred batch showed that, after reaction, the mixture contained 48 mole percent (R)-III, 2 mole percent unreacted (R)-I, and 50 mole percent unreacted (S)-I. Although the acetylation of the (R)-I epimer had proceeded with a yield of 96 percent, none of the (S)-I epimer in the original reaction mixture was acetylated under the reaction conditions, demonstrating the selectivity of the lipase enzyme. The acetylated product was separated from the unreacted alcohols by chromatographic methods using silica gel. The mixture was analyzed using a Hewlett Packard 1090 Series II liquid chromatograph equipped with a silica-based column (Phenomenex Kromasil 5 sil 100 A 250 mm×4.6 mm×5 μm) using hexane and THF as eluents. The gradient used for the separation was:

| Time (min) | Hexane (%) | THF (%) |
|---|---|---|
| 0 | 70 | 30 |
| 6 | 70 | 30 |
| 7 | 60 | 40 |
| 26.5 | 60 | 40 |
| 27 | 70 | 30 |
| 31 | 70 | 30 |

Under those elutions the (S)-I and (R)-I epimers are eluted at 20.6 minutes and 26.7 minutes, respectively, and the (S)-III and (R)-III epimers are eluted at 10.9 minutes and 11.16 minutes respectively. A chromatogram of compounds I and II is provided as FIG. 1.

Example 2

Comparative Example by a Non-Selective Reaction

For comparison, a non-selective reaction was run with a different enzyme in an immobilized form by introducing 10 mg (0.025 mmol) of an enriched mixture of the compound I epimers, containing 35 mole percent (S)-I and 65 mole percent (R)-I, into a vial with 0.03 ml (0.32 mmol) of vinyl acetate, 3 ml of MTBE, and 4.6 mg of CLEC-PC (cross-linked lipase from *Pseudomonas cepacia*, Altus, USA). The resulting batch mixture was stirred at room temperature for 48 hours. An HPLC analysis of the mixture showed that, after reaction, the batch contained 8 mole percent (S)-III, 6 mole percent (R)-III, 59 mole percent (R)-I, and 27 mole percent (S)-I. Acetylation of the (S)-I epimer proceeded with a yield of about 23 percent, and the acetylation if the (R)-I epimer proceeded with a yield of about 9 percent.

Example 3

Selective Acetylation of (S)-I and (R)-I Epimers Using *Alcaligenes* sp. Lipase

Selectivity was also found with an enzyme from *Alcaligenes* sp. lipase. The reaction was run by introducing 10 mg (0.025 mmol) of an enriched mixture of compound I epimers, containing 35 mole percent (S)-I and 65 mole percent (R)-I, with 0.03 ml (0.32 mmol) of vinyl acetate, 3 ml of MTBE, and 34 mg of lipase PL (*Alcaligenes* sp, Meito Sangyo, Japan). The resulting batch mixture was stirred at room temperature for 48 hours. After reaction, an HPLC analysis of the batch indicated the mixture contained 6 mole percent (R)-III, 59 mole percent (R)-I, and 35 mole percent non-reacted (S)-I. The acetylation of (R)-I proceeded with a yield of about 9 percent. However, as in example 1, none of the (S)-I reacted, demonstrating the selectivity of the enzyme.

Example 4

Selective Acetylation of (S)-I and (R)-I Epimers

Selectivity was also found using a high concentration of the (S)-I and (R)-I epimers at 50° C. with vinyl acetate as the solvent by introducing 188 mg (0.465 mmol) of an equimolar mixture of the (S)-I and (R)-I epimers into a vial with 188 mg (2.2 mmol) of vinyl acetate and 63 mg of *Pseudomonas stutzeri* lipase (TL, Meito Sangyo, Japan). The resulting batch mixture was stirred at 50° C. for 24 hours, and was found to contain 10.3 mole percent of (R)-III, 39.7 mole percent of unreacted (R)-I, and 50 mole percent unreacted (S)-I after reaction. The acetylation of (R)-I proceeded with a yield of about 21 percent. However, again, none of the (S)-I epimer was acetylated under the reaction conditions.

Example 5

Selective Acetylation of (S)-I and (R)-I Epimers

The selective acetylation of (R)-I using ethyl acetate as the acetylating agent was run by introducing 10.5 mg (0.026 mmol) of an enriched epimeric mixture, containing 35 mole percent of (S)-I and 65 mole percent of (R)-I, into a vial with 0.03 ml (0.32 mmol) of ethyl acetate, 4 ml of MTBE, and 20 mg of *Pseudomonas stutzeri* lipase (TL, Meito Sangyo, Japan). The resulting batch mixture was stirred at room temperature for 24 hours, and, upon HPLC analysis, was found to contain 4 mole percent (R)-III, 61 mole percent unreacted (R)-I, and 35 mole percent unreacted (S)-I. The acetylation of (R)-I proceeded with a yield of about 6 percent. However, again, none of the (S)-I epimer was acetylated under the reaction conditions.

Example 6

Selective Acetylation of (S)-I and (R)-I Epimers

The effect of the use of a different solvent was investigated by introducing 10.5 mg (0.026 mmol) of an enriched epimeric mixture, containing 35 mole percent of (S)-I and 65 mole percent of (R)-I, into a vial with 0.03 ml (0.32 mmol) ethyl acetate, 3 ml methyl ethyl ketone, and 100 mg of *Pseudomonas stutzeri* lipase (TL, Meito Sangyo, Japan), and stirring the resulting batch mixture at room temperature for 52 hours. An HPLC analysis of the resulting mixture showed that the batch contained 16.8 mole percent (R)-III, 48.2 mole percent unreacted (R)-I, and 35 mole percent unreacted (S)-I. The acetylation of (R)-I proceeded with a yield of about 26 percent. However, again, none of the (S)-I epimer was acetylated under the reaction conditions.

Example 7

Selective Alcoholysis of (S)-III and (R)-III Epimers

The selectivity of the alcoholysis of (R)-III and (S)-III was investigated by introducing 17.7 mg (0.039 mmol) of an equimolar mixture of (R)-III and (S)-III, 50 μl of ethanol, 3.5 ml MTBE, and 150 mg of *Pseudomonas stutzeri* lipase (TL, Meito Sangyo, Japan) into a vial, and stirring the batch mixture at room temperature for 124 hours. The HPLC analysis of a mixture produced by such a procedure indicated the mixture contained 4 mole percent (R)-I, 46 mole percent unreacted (R)-III, and 50 mole percent unreacted (S)-III. The alcoholysis of (R)-III proceeded with a yield of about 8 percent. However, none of the (S)-III epimer reacted under the reaction conditions.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

What is claimed:

1. A process for the selective conversion of the (R)-epimer substrate in a mixture comprising either:
    (a) (S)-I, (1S,5R,6R,7R)-6-[(3S)-3-hydroxy-5-phenyl-1-pentenyl]-7-[(4-benzoyl)oxy]-2-oxabicyclo[3,3,0]octan-3-one and (R)-I, (1S,5R,6R,7R)-6-[(3R)-3-hydroxy-5-phenyl-1-pentenyl]-7-[(4-benzoyl)oxy]-2-oxabicyclo[3,3,0]octan-3-one, or
    (b) (S)-III, (1S,5R,6R,7R)-6-[(3R)-3-acetoxy-5-phenyl-1-pentenyl]-7-[(4-benzoyl)oxy]-2-oxabicyclo[3,3,0]octan-3-one and (R)-III, (1S,5R,6R,7R)-6-[(3R)-3-acetoxy-5-phenyl-1-pentenyl]-7-[(4-benzoyl)oxy]-2-oxabicyclo[3,3,0]octan-3-one,
    wherein, for (a), the mixture is combined with an acetylating agent in the presence of a lipase to form an acetylation reaction mixture, wherein the (R)-I substrate is selectively converted to (R)-III, and, for (b), the mixture is combined with a $C_{1-6}$ alcohol in the presence of a lipase to form an alcoholysis reaction mixture, wherein the (R)-III substrate is selectively converted to (R)-I; and recovering the (S)-I substrate from 1(a) or recovering the (S)-III substrate from 1(b).

2. The process of claim 1, wherein the reaction mixture further comprises a solvent.

3. The process of claim 2, wherein the solvent is $C_2$ to $C_8$ linear, branched, or cyclic ether, $C_2$ to $C_8$ ketone, chlorinated $C_1$ to $C_4$ hydrocarbons, and tri($C_1$-$C_6$ alkyl)silyl groups.

4. The process of claim 3, wherein the solvent is selected from the group consisting of methyl tert-butyl ether (MTBE), diisopropyl ether, methyl ethyl ketone, dichloromethane, tetrachloromethane, acetone, methyl isobutyl ketone (MIBK), and THF.

5. The process of claim 4, wherein the solvent is MTBE or methyl ethyl ketone.

6. The process of claim 2, wherein the substrate is present in the solvent in an amount of from about 0.1 to about 20 weight/volume percent.

7. The process of claim 6, wherein the substrate is present in the solvent in about 0.1 to about 3 weight/volume percent.

8. The process of claim 1, wherein the (S)-I and (R)-I or (R)-III and (S)-III are in any ratio up to the solubility limit.

9. The process of claim 1, wherein the lipase is immobilized or crude.

10. The process of claim 1, wherein the lipase is selected from the group consisting of microbial, mammalian, and plant lipases.

11. The process of claim 10, wherein the lipase is isolated from at least one of *Candida antarctica, Pseudomonas* sp., *Pseudomonas cepacia, Alcaligenes* sp., *Pseudomonas stutzeri, Candida antarctica, Candida rugosa, Aspergillus niger*, and *Mucor meihei*.

12. The process of claim 11, wherein the lipase is isolated from *Pseudomonas cepacia* lipase, *Pseudomonas stutzeri* lipase or *Alcaligenes* sp lipase.

13. The process of claim 1, wherein the acetylation or alcoholysis reaction mixture is stirred for a period of time of from about 10 to about 250 hours.

14. The process of claim 13, wherein the acetylation reaction mixture is stirred for a period of time of from about 24 to about 60 hours.

15. The process of claim 14, wherein the acetylation reaction mixture is stirred for a period of time of from about 24 to about 52 hours.

16. The process of claim 13, wherein the alcoholysis reaction mixture is stirred for a period of time of from about 24 to about 250 hours.

17. The process of claim 16, wherein the alcoholysis reaction mixture is stirred for a period of time of from about 90 to about 160 hours.

18. The process of claim 1, wherein the acetylation or alcoholysis reaction mixture is stirred at a temperature of from about 10° C. to about 70° C.

19. The process of claim 18, wherein the acetylation or alcoholysis reaction mixture is stirred at a temperature of from about 25° C. to about 55° C.

20. The process of claim 1, wherein the acetylating agent is a $C_2$-$C_6$ alkyl acetate, $C_2$-$C_6$ alkenyl acetate or $C_5$-$C_8$ benzoyl acetate.

21. The process of claim 20, wherein the acetylating agent is selected from the group consisting of vinyl acetate, ethyl acetate, butyl acetate, vinyl butyrate and vinyl propionate.

22. The process of claim 1, wherein the $C_{1-6}$ alcohol is a $C_{2-5}$ alcohol.

23. The process of claim 22, wherein the $C_{1-6}$ alcohol is ethanol or butanol.

24. The process of claim 1, wherein the acetylating agent or $C_{1-6}$ alcohol and the substrate are present in a mole ratio of acetylating agent or alcohol to substrate of at least about 1:1.

25. The process of claim 24, wherein the acetylating agent or $C_{1-6}$ alcohol and the substrate are present in a mole ratio of acetylating agent or alcohol to substrate of from about 2:1 to about 3:1.

26. The process of claim 1, wherein the mixture in (a) further comprises reduced (R)-I, wherein both (R)-I and reduced (R)-I are selectively acetylated.

27. The process of claim 26, wherein the recovery of the (S)-I substrate or the (S)-III substrate is by chromatographic separation.

28. The process of claim 1, wherein the (R)-epimer is in reduced form.

29. The process of claim 1, wherein the (S)-I or (S)-III is in reduced form.

30. A process for the preparation of bimatoprost, comprising:
    a. selectively converting the (R)-I, (1S,5R,6R,7R)-6-[(3R)-3-hydroxy-5-phenyl-1-pentenyl]-7-[(4-benzoyl)oxy]-2-oxabicyclo[3,3,0]octan-3-one to (R)-III, (1S,5R,6R,7R)-6-[(3R)-3-acetoxy-5-phenyl-1-pentenyl]-7-[(4-benzoyl)oxy]-2-oxabicyclo[3,3,0]octan-3-one according to claim 1(a);
    b. recovering (S)-I; and
    c. converting (S)-I into bimatoprost.

31. A process for the preparation of bimatoprost, comprising:
    a. selectively converting (R)-III, (1S,5R,6R,7R)-6-[(3S)-3-acetoxy-5-phenyl-1-pentenyl]-7-[(4-benzoyl)oxy]-2-oxabicyclo[3,3,0]octan-3-one to (R)-I, (1S,5R,6R,7R)-6-[(3R)-3-hydroxy-5-phenyl-1-pentenyl]-7-[(4-benzoyl)oxy]-2-oxabicyclo[3,3,0]octan-3-one according to claim 1(b);
    b. recovering (S)-III;
    c. converting (S)-III into (S)-I; and
    d. converting (S)-I into bimatoprost.

* * * * *

UNITED STATES PATENT AND TRADEMARK OFFICE
CERTIFICATE OF CORRECTION

PATENT NO. : 7,611,886 B2 Page 1 of 1
APPLICATION NO. : 11/369518
DATED : November 3, 2009
INVENTOR(S) : Effenberger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 602 days.

Signed and Sealed this

Fourteenth Day of December, 2010

David J. Kappos
*Director of the United States Patent and Trademark Office*